US00PP30033P3

(12) United States Plant Patent
Avent

(10) Patent No.: US PP30,033 P3
(45) Date of Patent: Dec. 25, 2018

(54) ***HOSTA* PLANT NAMED 'SUN MOUSE'**

(50) Latin Name: ***Hosta* hybrid (Tratt.)**
Varietal Denomination: Sun Mouse

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 11 days.

(21) Appl. No.: 15/530,298

(22) Filed: Dec. 20, 2016

(65) Prior Publication Data

US 2018/0177096 P1 Jun. 21, 2018

(51) Int. Cl.
*A01H 5/12* (2018.01)
*A01H 5/02* (2018.01)

(52) U.S. Cl.
USPC ..... Plt./353
CPC ..... *A01H 5/02* (2013.01)

(58) Field of Classification Search
USPC ..... Plt./353
CPC ... A01H 5/12; A01H 5/02; A01H 5/00; A01H 5/0272; A01H 6/56
See application file for complete search history.

(56) References Cited

PUBLICATIONS

Common Wealth Nurseries ProNur Perennial list 3 2016, retrieved on Jan. 11, 2018, retrieved from the Internet at http://www.comnur.com/pronur_availabilty3.htm, pp. 1-4. (Year: 2016).*

* cited by examiner

*Primary Examiner* — June Hwu

(57) ABSTRACT

A new and distinct *Hosta* plant named 'Sun Mouse' with leaves that are slightly wavy thick substance and with golden coloration that holds up well through the season. The flowers are dark lavender bells tightly congested just above the foliage on chartreuse scapes with red blushing near base. 'Sun Mouse' has excellent vigor with rapid production of divisions, and its compact habit makes it useful in the miniature garden, as edging or front of the landscape border, in containers, as a specimen or en masse.

1 Drawing Sheet

Botanical classification: *Hosta* hybrid (Tratt.).
Variety denomination: 'Sun Mouse'.

BACKGROUND AND ORIGIN OF THE PLANT

The present invention relates to a new and distinct *hosta* plant, *Hosta* 'Sun Mouse' hereinafter also referred to as the new plant or by the cultivar name, 'Sun Mouse'. *Hosta* 'Sun Mouse' was hybridized by Tony Avent as a cross between the unreleased proprietary hybrid known only by the breeder code 2005-058 (not patented) as the female parent and the unreleased proprietary hybrid known only by the breeder code 2004-316 (not patented) as the male parent at a nursery in Raleigh, N.C., USA during the summer of 2006. The new plant was assigned the breeder code 2007-0655 and passed the initial evaluation in the summer of 2013 and has been asexually propagated by division at the same nursery in Raleigh USA since 2013 and also by careful shoot tip plant tissue culture with the resultant asexually propagated plants having retained all the same traits as the original plant. *Hosta* 'Sun Mouse' is stable and reproduces true to type in successive generations of asexual reproduction.

*Hosta* 'Sun Mouse' has not been made publically available until it was listed for sale Dec. 31, 2015. Any public disclosure of 'Sun Mouse' has been by the inventor, or one who obtained the material either directly or indirectly from the inventor, and any such disclosure has not been made more than one year prior to the application of this invention.

There are nearly 5,700 registered *hostas* with The American *Hosta* Society, which is the International Cultivar Registration Authority for the genus *Hosta* and a similar number of unregistered cultivars. The most similar *hosta* cultivars known to the applicant are *Hosta* 'Giantland Mouse Cheese' (not patented), 'Giantland Sunny Mouse Ears' (not patented) and 'Solar Mouse' (not patented). The new plant differs from 'Giantland Mouse Cheese' in that the habit and foliage size are much smaller on the new plant. Compared to 'Giantland Sunny Mouse Ears' the new plant has similar color, but the new plant is more compact. Compared with 'Solar Mouse' the new plant has better yellow foliage and maintains the yellow coloring through the entire growing season rather than becoming green as the situation with 'Solar Mouse', the new plant is more compact in habit and has smaller foliage. Compared with 'Blue Mouse Ears' (not patented) the new plant has golden foliage and not the green to blue-green coloration, but the stature is very similar. Compared with 'Mini Skirt' U.S. Plant Pat. No. 26,743 the new plant has golden foliage and darker lavender flower color.

Compared to 'Sun Mouse' the female parent has more pointed narrow dull chartreuse leaves and a 76 cm tall scape. The male parent differs in being taller and having green foliage.

Other *Hosta* cultivars have a compact short habit, yellow foliage of a similar nature, or other individual traits similar to 'Sun Mouse' but the new plant differs from the above listed cultivars and all other *hostas* known to the applicant, by the combination of the following traits.

1. Excellent vigor with rapid production of divisions.
2. Leaves are slightly wavy with golden coloration and thick substance.
3. Foliage color emerges golden and holds the color well throughout the season.

4. Compact habit and useful in the miniature garden, as edging or front border, as a specimen or en masse of the landscape.
5. Flowers just above foliage of light purple bells on chartreuse scapes with strong-purple speckling to blushing near base.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
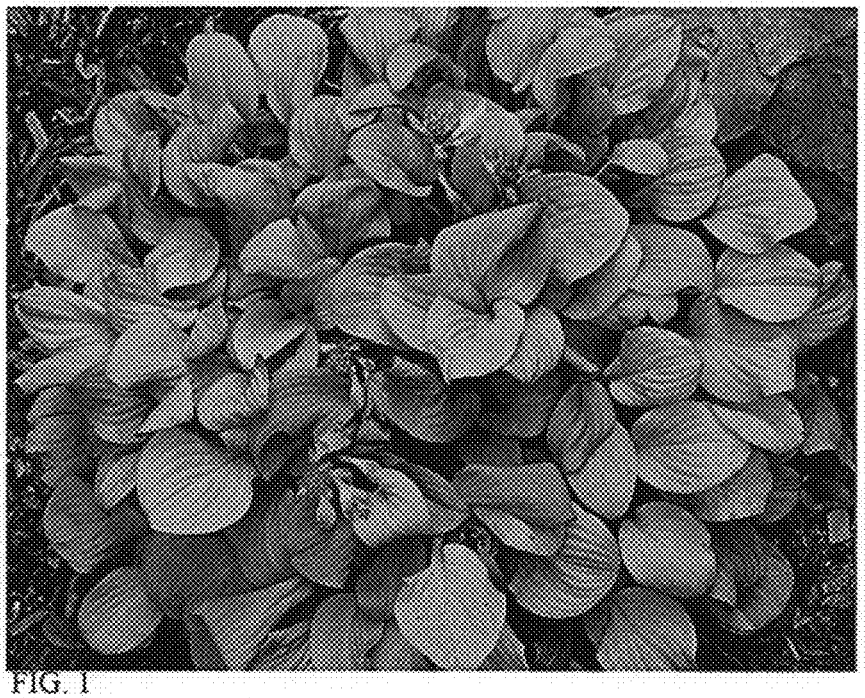
FIG. 1 shows a nine-year old plant in a partly-shaded garden at a nursery in Raleigh, N.C. with supplement water as needed.
Figure 2:
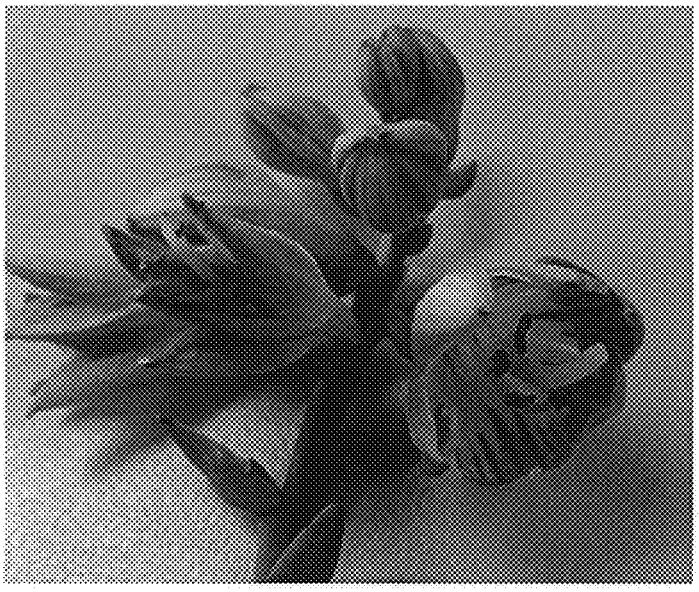
FIG. 2 shows a close-up of a typical flower scape.

The following descriptions and color references are based on the 2001 edition of The Royal Horticultural Society Colour Chart except where common dictionary terms are used. The new plant, *Hosta* 'Sun Mouse', has not been observed under all possible environments. The phenotype may vary slightly with different environmental conditions, such as temperature, light, fertility, moisture and maturity levels, but without any change in the genotype. The following observations and size descriptions are of a nine-year-old plant in a garden in Raleigh, N.C. with supplemental water as needed.

Botanical classification: *Hosta* x hybrid;

Parentage: Female or seed parent—unreleased proprietary hybrid 2005-058 (not patented); male or pollen parent—unreleased proprietary hybrid 2004-316 (not patented);

Propagation: Garden division and sterile plant tissue culture;

Time to initiate roots from tissue culture: About two to three weeks;

Growth rate: Vigorous;

Crop time: About three months to finish during the spring in a one-liter container from rooted tissue culture plantlet;

Rooting habit: Fleshy, lightly branching;

Plant shape and habit: Hardy herbaceous perennial with basal rosette of leaves emerging from rhizomes producing a short, compact, symmetrical mound of small upright to arching leaves;

Plant size: Foliage height about 15.0 cm above soil line to the top of the leaves and about 30.0 cm wide at the widest point just above soil line;

Foliage description: Glabrous, glaucous adaxial, slightly lustrous abaxial; oblong to oval; acuminate apex, oblique to cordate base; margin entire; slightly sinuate with three to five undulations;

Leaf blade size: About 7.6 cm long and 5.1 cm wide;

Leaf blade color: Early season and expanding adaxial variable with light exposure, from nearest RHS N144A and RHS 151D to RHS 144A; early season abaxial between RHS N144A and RIM 145A; mid-season and later summer adaxial variable with light intensity, from nearest RHS 144A to nearest RHS 151D; mid-season and later adaxial lighter than RHS 146D to nearest RHS 144A;

Petiole: Glabrous, slightly glaucous adaxial and slightly lustrous abaxial, concavo-convex; stiff; 7.6 cm to 11.4 cm long and 8.0 to 9.5 mm wide at base, average about 6.5 cm long and 9.0 mm wide;

Petiole color: Adaxial and abaxial margins blend between RHS 146D and RHS N144A with purplish speckling at base of nearest RHS 83C; abaxial midrib of nearest 145D;

Veins: Five to seven pairs and midrib; parallel; slightly raised on abaxial side;

Veins color: Adaxial vary between nearest RHS 144A and RHS 144C depending on light exposure; abaxial veins nearest RHS 144A to the same color as the surrounding tissue;

Flower description:

Inflorescence: Raceme; average about 20.0 cm tall; flowering portion about 6.0 cm long and 4.5 cm wide;

Buds one day prior to opening: Clavate to globose with rounded apex and narrow base; about 0.8 cm in diameter at widest with base narrowing at about mid-length to about 0.4 cm diameter; about 2.3 cm long;

Bud color: Between blend RHS 85A and RHS 91B and RHS 91C with veins of nearest RHS 85C;

Flowers: Perfect; single; perianth shape campanulate funnelform; held nearly horizontal with pedicel at 90 degree angle to peduncle; corolla tube about 2.5 cm wide and 3.5 cm long, (distal flowers smaller), persists for a normal period, usually one day on plant or as cut flower; scapes remain effective with flowers beginning early June for about two weeks; with about 20 flowers per scape; no detectable fragrance;

Tepal: Two nearly identical sets of three, glabrous, entire margins; fused at base; clavate with broadly acute apex; each approximately 2.8 cm long and 1.0 cm wide;

Tepal color: Coloring of both sets identical except inner set with 1.0 mm wide translucent margin; abaxial basal one third (corolla tube) near white, lighter than RHS 155D, abaxial center to apex lighter than RHS N82D with veins of nearest RHS N82C; adaxial basal one quarter white, lighter than RHS 155D, adaxial distal three quarters nearest RHS N82C with three main veins of nearest RHS N82A;

Gynoecium: Single;

*Style*.—Single, terete; approximately 3.0 cm long, 1.2 mm diameter, curved upward slightly in distal 2.0 mm; color nearest RHS 155D distally with base nearest RHS 145A.

*Stigma*.—Tri-lobed, about 1.0 mm in diameter; color nearest RHS 155D.

Androecium:

*Filaments*.—Six, approximately 3.0 cm long and 1.0 mm in diameter, curved upward to nearly 90 degrees in the apical 4.0 mm; color nearest RHS 155D.

*Anthers*.—Elliptic; dorsifixed, longitudinally dehiscent; about 2.5 to 3.5 mm long, 1.5 mm wide; color between RHS N199A and RHS N199B.

*Pollen*.—Elliptic, less than 0.1 mm long; color nearest RHS 16A.

Peduncle: Usually one per mature division; glaucous, glabrous; nearly vertical; about 25.0 cm tall, and about 4.5 mm in diameter at base;

Peduncle color: Nearest RHS 144A with speckled to blushed with nearly solid strong-purple nearest RHS 83C in the lower portion;

Pedicel: Short, glabrous; slightly glaucous; terete; about 10.0 mm long and 1.3 mm diameter;

Pedicel color: Nearest RHS 160C with tinting of nearest RHS 182A;

Scape and floral bracts: Each flower normally subtended by a single bract with one or two below lowest flower; lanceolate; acute apex and truncate base; entire margin; glabrous matte surface abaxial and adaxial; decreasing in size distally; average about 10.0 cm long 5.5 mm wide; attitude outright;

Bract color: Adaxial and abaxial blend nearest RHS 144A with speckling of nearest RHS 182A in high light exposure;

Fruit: Not yet observed;

Seed: Not observed; probably sterile under present growing conditions;

Disease resistance: The new plant has not shown any resistance to pests and diseases common to *hostas*. The plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3a through 8b, and other disease resistance is typical of that of other *hostas*.

It is claimed:

1. A new and distinct ornamental plant cultivar named *Hosta* 'Sun Mouse' as herein described and illustrated.

* * * * *